United States Patent [19]

Edwards et al.

[11] Patent Number: 5,523,081
[45] Date of Patent: Jun. 4, 1996

[54] SHAVING COMPOSITION

[75] Inventors: Christopher J. Edwards; Cameron W. Jones, both of Leeds, United Kingdom

[73] Assignee: Chesebrough-Pond's USA Co., Division of Conopco, Inc., Greenwich, Conn.

[21] Appl. No.: 292,679

[22] Filed: Aug. 18, 1994

[30] Foreign Application Priority Data

Aug. 18, 1993 [GB] United Kingdom ............... 9317177
Mar. 28, 1994 [GB] United Kingdom ............... 9406119

[51] Int. Cl.⁶ .................................................. A61K 7/15
[52] U.S. Cl. ........................... 424/73; 424/70.12; 424/47
[58] Field of Search ............................. 424/73, 70.12

[56] References Cited

U.S. PATENT DOCUMENTS

| 3,541,581 | 11/1970 | Monson | 252/90 |
| 4,957,732 | 9/1990 | Grollier et al. | 424/73 |
| 5,104,643 | 4/1992 | Grollier et al. | 424/47 |

FOREIGN PATENT DOCUMENTS

| 0138192 | 10/1983 | European Pat. Off. . |
| 0268982 | 6/1988 | European Pat. Off. . |
| 0270249 | 6/1988 | European Pat. Off. . |
| 0514934 | 11/1992 | European Pat. Off. . |
| WO91/07943 | 6/1991 | WIPO . |

Primary Examiner—Thurman K. Page
Assistant Examiner—James M. Spear
Attorney, Agent, or Firm—Milton L. Honig

[57] ABSTRACT

The invention pertains to a cosmetic composition intended for shaving of the skin in aerosol or post-foaming gel form comprising water, soap, an inert volatile liquid agent, optionally a gelling agent, and a polyorganosiloxane microemulsion having an average particle size of less than 0.14 microns.

7 Claims, No Drawings

SHAVING COMPOSITION

BACKGROUND OF THE INVENTION

1. Field of the Invention

The present invention relates to cosmetic compositions. In particular, it relates to cosmetic compositions intended for shaving of the skin which comprise polyorganosiloxanes.

2. The Related Art

Such shaving products can be creams or can be dispensed from a suitable package as an aerosol foam or a post-foaming gel. The present invention is particularly concerned with the latter types of products which can be dispensed from a valved container adapted to maintain the product under pressure and dispense it when desired by opening the valve.

Aerosol-foam shaving compositions are normally contained in a single-compartment dispenser with the inert volatile liquid agent as the propellant gas in accordance with conventional aerosol technology.

Post-foaming gel shaving compositions can be packaged in many types of containers which are commercially available. Where aerosol dispensers are employed, generally the gel is maintained in a package separate from the propellant by means of a conventional 'bag in can' packaging system or a diaphragm inside the package driven by a propellant or a mechanical force, such as a spring. Suitable dispenser forms are described in e.g. U.S. Pat. No. 3,541,581.

The use of polyorganosiloxanes in shaving compositions is well known. Their function is to alleviate shaving rash and generally improve lubrication and softness of skin. Typical examples of shaving compositions with polyorganosiloxanes can be found in U.S. Pat. No. 4,957,732, U.S. Pat. No. 5,104,643 and WO 91/07943.

In U.S. Pat. No. 4,957,732 shaving compositions, in particular of the aerosol type, are described which include a polyorganosiloxane containing a specific acyloxyalkyl group. Improved stability, smoothness and hair-cutting benefits are claimed.

In U.S. Pat. No. 5,104,643 shaving compositions, both aerosol and gel-type products, are described which include a polyorganosiloxane containing a specific hydroxyalkyl group. Again stability, smoothness and hair-cutting benefits are claimed.

In WO 91/07943 a post-foaming shaving gel is described comprising a polysiloxane polyether copolymer. Clarity and brightness effects are claimed.

Whilst these shaving products represent a popular form of pre-shaving treatment, there is scope for improving their aesthetic and sensory properties. In particular, there is scope for improvement of the properties of these compositions with regard to the lubrication that they provide to the blade whilst shaving, the foam quality, and also the feel of the skin after the shaving process.

It is an object of this invention to improve on these, and other problems associated with the prior art compositions.

SUMMARY OF THE INVENTION

It has been found that the use of polyorganosiloxanes in micro-emulsion form of relatively small particle size has a very beneficial effect on the lubrication properties of the shaving foam, the richness and stability of the foam during shaving whilst having good foam-rinsability and valve anti-clogging behaviour, and skin-feel after shaving.

Thus, according to the invention, there is provided a cosmetic composition intended for shaving of the skin comprising from 40–90% by weight of water, from 4–25% by weight of water-soluble soap, from 0.5–12% by weight of an inert volatile liquid agent, and optionally from 0.01–5% by weight of water-soluble gelling agent, characterised in that the composition further comprises 0.01–15% by weight of a polyorganosiloxane micro-emulsion, the micro-emulsion having an average particle size of less than 0.14 microns.

The inclusion of the polyorganosiloxane micro-emulsion having an average particle size of less than 0.14 microns will accord to the compositions superior properties in terms of the lubrication experienced by the user during the shaving process, and the feel of the skin after the shaving process is complete as well as providing a very creamy rich foam and improved razor glide.

DETAILED DESCRIPTION

The essential components of the composition according to the invention will now be described in further detail below.

The water in the composition of the present invention may be tap water, distilled water or deionised water. The composition should comprise from 40–90% by weight of water, more preferably from 50–80% by weight of water. The upper limit of water in the composition may be determined by the maximum amount that will produce a satisfactory gel or foam in use.

In addition, the composition may optionally comprise small amount of polar substances, such as low molecular weight alcohols, methanol, ethanol, propanol, and isopropanol, provided that these do not detract from the overall properties of the composition. These may advantageously generate a cooling effect on the skin during the shaving process.

The soap used in the composition according to the invention may be any soap which is known in the art, and which may be prepared in a conventional manner. It has however been found that the type of soap used in the composition may alter the characteristics of the gel or foam produced. To this end, preferred soaps include the water soluble stearate and palmitates soaps, such as potassium, ammonium, sodium, and the soluble amine soaps of commercial stearate acid and palmitic acid. Such soaps may typically be made by neutralisation of the appropriate higher fatty acid with suitable alkali, or may be introduced in the form of animal or vegetable fats which are rich in the appropriate acid, and which, when saponified, form soaps rich in the corresponding acid. Mixtures of the various soaps may also be used.

In general, lathers comprising animal fats soaps, or animal fat and vegetable fat soaps, are preferred.

Preferably, from 30–100% of the soap used in the composition is a water-soluble stearate, more preferably from 60–100% by weight of the soap is a water-soluble stearate.

The composition according to the invention may optionally comprise a wetting agent. Typical wetting agents include triethanolaminelauryl sulphate, sodium lauryl sulphate, sodium dodecyl benzene sulphonate, water-soluble polyoxyethylene ethers of alkyl substituted phenols, and water-soluble polyoxyethylene cetyl ethers. The wetting agent in the composition may be effective in facilitating the rinsing of the lather from the skin. If used, preferably the wetting agent is present in the composition at a level of from 0.5–6% by weight.

Preferably, the total amount of soap (including any wetting agent) used in the composition according to the invention is from 4–25%, more preferably from 5–20%, most preferably from 10–18% by weight of the total composition.

The gelling agents used in compositions of the post-foaming gel type according to the invention are typically water-soluble derivatives of naturally occurring substances such as cellulose, sucrose, and glucose. Preferred gelling agents include the co-polymers of acrylic acid and a polyally sucrose, and reaction products of cellulose or glucose with acids or alkaline oxides.

The gelling agents may be used in the composition at a level of 0.01–5% more preferably 0.01–2.5%, most preferably 0.05–1.5% by weight of the total composition.

Suitable acrylate derivatives include the Carbopol (trademark) range of polymers. Cellulose derivatives are however preferred, since these provide good lubrication for the shaving blade as well as functioning as a gelling aid. Suitable cellulose derivatives include sodium carboxymethyl cellulose, cellulose methylether, and hydroxy alcohol cellulose. Particularly preferred cellulose derivatives are the commercially available products Natrosol and Klucel (trademarks). These may typically be used at a level of 0.01–0.4% by weight.

The inert volatile liquid agent as used in the aerosol form of the composition of the present invention should be suitable to function as an aerosol propellant gas, and can be selected from a wide variety of the propellants known in the aerosol industry. Suitable selections include inert inorganic gases such carbon dioxide, nitrogen, argon and air.

However, in general more uniform foaming is achieved by selection from lower hydrocarbon or wholly or partially halogenated hydrocarbon liquefied propellants. They are usually emulsified in the aqueous phase of the compositions.

Suitable examples of liquid or liquefied propellant agents include saturated aliphatic hydrocarbons having from 1 to 4 carbon atoms. They can be unhalogenated such as propane, n-butane and iso-butane, or halogenated with fluorine or chlorine, such as monochlorotrifluoromethane, dichlorodifluoromethane, trichloromonofluoromethane, and similar chlorofluorohydrocarbons preferably with from 1 to 3 carbon atoms. Also mixtures of hydrocarbons and halogen-substituted hydrocarbons can be used. The post-foaming gel of the current invention comprises the water-soluble gelling agent and the inert volatile liquid agent as post-foaming agent. It needs to be appropriately packaged such that when the gel is stored for prolonged periods, it remains as a stable homogenous composition. However, on being dispensed, it should remain substantially free of foaming until it is appropriately activated, for example by manual shearing.

Preferably, the gel composition has a yield value sufficiently high to substantially restrain the composition from foaming for at least 60 seconds under static ambient conditions.

The post-foaming gels of the current invention are coherent colloidal dispersions of at least four base components, including water, a gelling agent, soap, and a post-foaming agent, in addition to the polyorganosiloxane micro-emulsion. They will generally exhibit mechanical properties characteristic of the solid state, and will comprise matrix of homogeneously dispersed components and medium. Typically, the gels of the invention have a yield value; that is they resist flow up to a given sheering tension, and then behave as an elastic solid below that tension. They are typically formed from a solution, as opposed to being formed from a solid substance which exhibits swelling power. In order that stable gel can be formed from solution, it is necessary that a solid substance separates from a solution in a finally dispersed colloidal state, and the separated solid particles are neither deposited by gravity nor remain in a colloidal suspension as freely moving kinetic units. Rather, they join together to form a continuous coherent framework, throughout the mass of the solution.

As the post-foaming agent for use in the gel compositions of the present invention the inert volatile liquid should be capable of being dispersed continuously throughout the stable gel, and compatible with other components of the gel. The vapour pressure of the post-foaming agent is also critical, in that a lather should be produced by volatilisation of the post-foaming agent when the gel is rubbed between the fingers or on the skin. Additionally, when the gel is dispensed from the storage container, it should remain free from foaming for at least 60 seconds.

Suitable such post-foaming agents for use in the gel compositions according to the invention are liquids or liquefiable, and include saturated aliphatic hydrocarbons having from 4–6 carbon atoms, such as butanes, pentanes and hexanes (in particular isopentane and isobutane). Other suitable post-foaming agents include partially or wholly halogenated hydrocarbons, such as trichlorotrifluoro ethane. Also, mixtures of aliphatic and halogenated hydrocarbon propellants or post-foaming agents can be used. Generally, suitable post-foaming agents are those substances which have a low solubility in water, for example less than about 20 cc of gas in 100 grams of water at one atmosphere and 20° C.

The amount of inert volatile agent used in the compositions of the present invention may have an important effect on the properties of the composition, including the stability of foam, the yield value, post-foaming characteristics of the gel compositions, and the foam profile. The amount of volatile agent whether as propellent or post-foaming agent may however routinely be varied by the skilled man to optimise the desired characteristics of the gel or the foam.

Aliphatic hydrocarbon volatile agents would typically comprise 0.5–4% by weight of the composition, more preferably 1.5–3.5% by weight. Halogenated hydrocarbon agents would typically comprise from 1 to 12%, more preferably, from 1–8% by weight and most preferably, from 3–7% by weight of the composition.

The polyorganosiloxane micro-emulsion used in the composition according to the invention may be any micro-emulsion with an average particle size of less than 0.14 microns, most preferably in the region 25–50 nm. Such a micro-emulsion imparts to the composition benefits in terms of the improved sensory properties described above. However, it also does not cloud the shaving composition, permitting a substantially clear composition, since the micro-emulsion is itself substantially optically clear.

Suitable polyorganosiloxane micro-emulsions for use in compositions according to the invention include modified amino alcohol substituted polydiorganosiloxanes, such as are described in U.S. Pat. Nos. 4,749,732 and 4,620,878, and the polydiorganosiloxane micro-emulsion described and referred to in EP 0 268 982, which may be produced by emulsion polymerisation. Also, the micro-emulsion organo-silicone compounds described in U.S. application Ser. No. 481,033, filed Feb. 16, 1990, U.S. Pat. No. 5,015,682 and assigned to Dow Corning Corporation, may be suitable, these being selected from the group consisting of carboxy glycol ether and carboxy glycol ester functional polysiloxanes. The content of all of these applications is incorporated herein by reference.

Also, polyorganosiloxanes for use in compositions according to the invention may include those described in EP 0 514 934, the content of which is incorporated herein by reference, which are non-polar insoluble aminofunctional polydiorganosiloxane micro-emulsions. Such micro-emulsions are optically clear, and provide beneficial properties to the compositions of the invention.

Preferred polyorganosiloxanes for use in compositions according to the invention are micro-emulsified polydialkyl siloxanes, in particular polydimethyl siloxanes. Preferred polydialkyl siloxanes may be made by micro-emulsion techniques such as are described in EP 0 268 982, the content of which is incorporated herein by reference, and are hydroxy terminated polymerised dialkyl siloxanes having a particle size is less than 0.14 microns. Preferred polydialkyl siloxanes have a relatively high molecular weight, in the region 60000–90000 amu, and have the corresponding kinematic viscosity.

A particularly preferred micro-emulsion for use in compositions according to the invention is the preprepared micro-emulsion composition DC2-1865, made by Dow Corning. This micro-emulsion has a pH in the region 6.0–7.5, and an average particle size in the region 27–40 nm. The composition may have a corresponding kinematic viscosity of 10,000–30,000 cps, more preferably 12,000–20,000 cps. The pre-prepared micro-emulsion typically comprises 22% by weight of OH terminated polydimethyl siloxane, 3% cyclomethicone, 14% triethanolamine dodecyl benzene sulphonate, 4% polyethylene oxide lauryl ether, 0.3% potassium sorbate as a preservative, and the balance water.

Such micro-emulsion compositions may be made by methods described in EP 0 265 982, for example as described in example 2.

To this end, water, dodecyl benzene sulphonate, and cyclic dimethyl siloxane tetramet may be made into a crude emulsion. Separately, water, dodecyl benzene sulphonate and polyethylene oxide lauryl ether may be made into an aqueous solution and stirred gently at 80° C., with emulsion polymerisation being carried out by gradually adding the crude emulsion dropwise to the aqueous dodecyl benzene sulphate solution. The mixture is then cooled, maintained at 40°–50° C. for two hours, and adjusted to pH 7 using triethanolamine. The emulsion may be broken by using methanol to extract the oil, with some residual unreacted cyclomethicone being left in the equilibrium mixture.

The molecular weight of the polydimethyl siloxane produced in the micro-emulsion can be varied by adjusting the temperature of the dodecyl benzene sulphonate solution to which the crude emulsion is added. Typically the temperature may be varied in the region 10°–80° C., which results in polydimethylsiloxane having a kinematic viscosity in the region 10,000–200,000 cps, the higher temperature reaction producing the lower viscosity polydimethylsiloxane.

Other methods which may be used for making polyorganosiloxanes micro-emulsions which may be used in compositions according to the invention include those described in EP 0 228 575 referred to above, the disclosure of which is incorporated herein by reference. This describes a method of making a stable micro-emulsion of high molecular weight silicone polymer and water by sequentially adding at an effective rate a standard emulsion comprising polydiorganosiloxane precursor, surfactant and water to a polymerization catalyst medium while mixing to form a clear, stable aqueous micro-emulsion of polydiorganosiloxane.

An alternative method of making a micro-emulsion for use in compositions according to the invention may be a mechanical emulsification technique, wherein the polyorganosiloxane, stabilising surfactant and water are simply mixed together and homogenised using conventional milling apparatus to achieve the desired particle size. Such emulsification techniques per se are well known in the art.

Another method of making suitable micro-emulsions for use in the invention are described in EP 0 138 192, the disclosure of which is also incorporated herein by reference.

The polyorganosiloxane is preferably a liquid at ambient temperatures, so as to be of a suitable viscosity to enable it to be readily emulsified with the required particle size of 0.14 microns or less. However, high viscosity or even solid materials may also be used if dissolved in a water-immiscible solvent. For example, in the case of a polyorganosiloxane which is highly viscous, a suitable solvent is a volatile silicone or a volatile hydrocarbon. Examples of such compositions are known and documented in the patent literature.

The polyorganosiloxane micro-emulsions should be present in the compositions according to the present invention in an amount from 0.01–15% percent by weight, more preferably from 0.1 to 5% by weight of the total composition.

The products according to the invention may additionally comprise other optional ingredients, such as humectant, skin fresheners, lather stabilisers, colouring materials, dyes, perfumes, preservatives, bactericides, bacteriostats and other components routinely used in such compositions.

Preferred additional components of the composition are polymeric deposition systems, such as cationic deposition polymers. Especially preferred are cationic derivatives of guar gum, or cationic cellulose ether derivatives.

Suitable cationic guar gum derivatives are those given the CTFA designation guar hydroxypropyl trimonium chloride, available commercially for example as JAGUAR C13S, which has a low degree of substitution of the cationic groups and high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR 162 which is a high transparency, medium viscosity guar having a low degree of substitution.

Suitable cationic cellulose ether derivatives are quaternary ammonium derivatives of cellulose ethers, for example the Polymer JR series of materials available from Union Carbide.

The deposition polymer may be present in an amount of from 0.01 to 10% by weight of the total composition, preferably from 0.01 to 1% by weight, even more preferably from 0.04 to 0.5% by weight.

EXAMPLES

The invention will now be described by way of example.

A shaving gel composition according to the following composition was made up, and tested for its sensory and aesthetic properties.

Example 1

| | % w/w |
|---|---|
| Propylene Glycol | 1.5 |
| Palmitic Acid | 8.0 |
| Stearic Acid | 2.8 |
| Ceteth-2 (Brij 52) | 0.8 |
| Triethanolamine | 6.1 |
| DC2-1865 silicone micro-emulsion (ex Dow Corning) | 2.0 |
| Fragrance | 0.4 |
| Sorbitol | 2.5 |
| Sodium isostearoyl lactylate | 0.1 |
| Hydroxyethylcellulose | 0.25 |
| Hydroxypropylcellulose | 0.2 |
| Isopropane/Isobutane | 3.0 |
| water | to 100 |

The composition may be manufactured by charging a polymer vessel with the sorbitol. The hydroxyethyl- and-propylcellulose are added with stirring until the mixture is dispersed and homogenous. One third of the water is slowly added to this, and the mixture left to gel.

A main mixing vessel is then charged with one third of the water, and heated to 80° C. To this is added stearic and palmitic acids with stirring, until the mixture has melted. The composition is maintained at 80° C. whilst the Ceteth-2 and Propylene glycol are added.

Meanwhile the remaining ingredients except the fragrance and isopropane/isobutane are premixed in a side pot, and added to the main mixing vessel with stirring, whilst retaining the temperature at 80° C., until the mixture is a homogenous solution. The mixture is then cooled to 35° C. with stirring, when the polymer solution is mixed in until the solution is homogenous. The perfume is then mixed in until the solution is homogenous. The solution can then be centrifuged if necessary, and filled with the isopropane/isobutane gas into appropriate package in a conventional manner.

Comparative Test

The gel formulation of example 1 was tested against a similar composition which did not contain the DC2-1865 micro-emulsion, and instead contained an extra 2% water. The compositions were tested on a panel of 12 people, who are regular wet shavers, and who applied one composition to one side of the face for the test and the other composition to the other side of the face.

Eleven out of the twelve panel testers preferred the composition containing the DC-1865 micro-emulsion, citing as their reason for the preference richer, a creamier foam with greater volume, improved razor glide and smooth skin after-feel.

Example 2

The following compositions represent post foaming shaving gels according to the invention, which can be prepared according to a method analogous to that described in example 1.

| Component | (2a) % w/w | (2b) % w/w |
|---|---|---|
| Propylene Glycol | 1.5 | 1.5 |
| Palmitic Acid | 8.0 | 8.0 |
| Stearic Acid | 2.8 | 2.8 |
| Propylene Glycol Isostearate | — | 1.0 |
| Ceteth-2 | 1.0 | 1.0 |
| Triethanolamine | 6.1 | 6.1 |
| DC2-1865 silicone micro-emulsion (ex Dow Corning) | 2.0 | 1.0 |
| Fragrance | 0.6 | 0.9 |
| Sorbitol | 2.5 | 2.5 |
| Hydroxyethylcellulose | 0.25 | 0.25 |
| Hydroxypropylcellulose | 0.02 | 0.02 |
| Isopropane/Isobutane | 3.0 | 3.0 |
| Dye | trace | trace |
| Water | to 100 | to 100 |

Example 3

The following compositions represent two aerosol shaving foams compositions according to the invention, which can be prepared according to a method analogous to that described in example 1.

| Component | (3a) % w/w | (3b) % w/w |
|---|---|---|
| Stearic Acid | 3.3 | 3.3 |
| Palmitic Acid | 3.5 | 3.5 |
| Lauric Acid | 0.8 | 0.8 |
| Triethanolamine | 3.0 | 3.0 |
| DC2-1865 silicone micro-emulsion (ex Dow Corning) | 2.0 | 1.5 |
| DC 193 silicone (dimethicone copolyol ex Dow Corning) | — | 0.8 |
| Fragrance | 0.7 | 0.7 |
| Potassium Hydroxide (50%) | 0.5 | — |
| Potassium Hydroxide (flakes) | — | 0.3 |
| Cocamidopropyl Betaine | 0.4 | 0.4 |
| Glycerine | 4.6 | 4.6 |
| Minerol Oil | 2.0 | 1.3 |
| Menthol | 0.2 | — |
| Polysorbate (Tween 20) | 1.0 | 1.0 |
| Butylated Hydroxy Toluene | 0.05 | — |
| Sodium isostearoyl lactylate | 0.1 | 0.1 |
| Butane/isobutane/propane mix | 4.0 | 4.0 |
| Water | to 100 | to 100 |

We claim:

1. A shaving composition comprising:
   (i) from 40–90% by weight of water;
   (ii) from 4–25% by weight of water-soluble soap;
   (iii) from 0.5–12% by weight of an inert volatile liquid agent;
   (iv) from 0.01–15% by weight of a polyorganosiloxane micro-emulsion having an average particle size of less than 0.14 microns, the microemulsion comprising polydimethyl siloxane, cyclomethicone and and dodecyl benzene sulphonate and the balance water; and
   (v) optionally from 0.01–5% by weight of water-soluble gelling agent.

2. The shaving composition of claim 1 wherein the polyorganosiloxane micro-emulsion has an average particle size within the range of from 25 to 50 nm.

3. The shaving composition of claim 1 which is a post-foaming shaving gel comprising of from 0.01–5% by weight of the water-soluble gelling agent and wherein the volatile liquid agent is a post-foaming agent.

4. The shaving composition of claim 3 wherein the gelling agent is selected from the group consisting of co-polymers of acrylic acid and a polyallyl sucrose, the reaction products of cellulose with acids, of glucose with acids, of cellulose with alkaline oxides, and of glucose with alkaline oxides.

5. The shaving composition of claim 1 which comprises of from 0.1 to 5% by weight of the polyorganosiloxane micro-emulsion.

6. The shaving composition of claim 1 which is an aerosol shaving foam composition and wherein the volatile liquid agent is an aerosol propellant gas.

7. A shaving composition comprising:
  (i) from 40–90% by weight of water;
  (ii) from 4–25% by weight of water-soluble soap;
  (iii) from 0.5–12% by weight of an inert volatile liquid agent;
  (iv) from 0.01–15% by weight of a polyorganosiloxane micro-emulsion having an average particle size of less than 0.14 microns, the microemulsion comprising 22% by weight of OH terminated polydimethyl siloxane, 3% cyclomethicone, 14% triethanolamine dodecyl benzene sulphonate, 4% polyethylene oxide lauryl ether, 0.3% potassium sorbate and the balance water; and
  (v) optionally from 0.01–5% by weight of water-soluble gelling agent.

* * * * *